US00PP12242P2

(12) United States Plant Patent
Hawks

(10) Patent No.: US PP12,242 P2
(45) Date of Patent: Dec. 4, 2001

(54) ECHINACEA PLANT NAMED 'KIM'S KNEE HIGH'

(75) Inventor: Kimberly Terry Hawks, Carrboro, NC (US)

(73) Assignee: Kimberly Terry Hanks, Chapel Hill, NC (US)

( * ) Notice: Subject to any disclaimer, the term of this patent is extended or adjusted under 35 U.S.C. 154(b) by 0 days.

(21) Appl. No.: 09/286,860

(22) Filed: Apr. 6, 1999

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database, 2000/04, GTI Jouve Retrieval Software, citation for 'Kim's Knee High'.*

* cited by examiner

*Primary Examiner*—Bruce R. Campell
*Assistant Examiner*—Susan B. McCormick

(57) ABSTRACT

*Echinacea purpurea* 'Kim's Knee High' is a new and distinct dwarf perennial Cone Flower with rose-pink to purple-pink flowers on plants 38 to 60 cm (15 to 24 inches) tall for an extended period of twelve weeks.

1 Drawing Sheet

BRIEF SUMMARY OF INVENTION

The present invention comprises a new and distinct cultivar of Coneflower, botanically know as *Echinacea purpurea*, and hereinafter referred to by the cultivar name 'Kim's Knee High'.

The new cultivar is valued for its unique and long-lasting flower display and short plant habit.

'Kim's Knee High' is a whole plant selection by Kim Hawks after crossing and evaluation of dwarf Coneflower for three generations at a nursery in Chapel Hill, N.C., starting with a chance seedling of unknown origin, from *Echinacea purpurea*. Kim has propagated this plant asexually by root cuttings, at the same nursery in Chapel Hill, N.C., and it has also been reproduced successfully by tissue culture. Rooting occurs in two to four weeks. Plants are finished off to flowering size in 10 to 12 weeks in three inch pots. The plant retains its distinctive characteristics and reproduces true to type individuals in successive generations.

BACKGROUND OF THE PLANT

*Echinacea purpurea* is an American native plant found in the eastern United States region normally bounded by Michigan and Oklahoma on the west and Virginia, North Carolina and Georgia on the east. These are several named varieties, including: 'Alba' (not patented), 'Bright Star' (not patented), 'Magnus' (not patented), 'Monk's Silver' (not patented), *Rudbeckia purpurea* plant U.S. Plant Pat. No. 2,414 (now known as *Echinacea purpurea* 'Robert Bloom' U.S. Plant Pat. No. 2,414), 'The King' (not patented), 'White Lustre' (not patented), and 'White Swan' (not patented), most of which are seed propagated. These are all taller varieties, like the straight species, that flower in heights varying between 65 and 150 cm (26 to 60 inches) tall. One dwarf variety, *Echinacea purpurea* 'Cygnet White' (not patented), is a selection with white horizontal ray florets that reaches 51 cm (20 inches) in plant height. Other short forms exist, such as 'Nana' (not patented) in Great Britain and 'Rosenelf' (not patented) in Germany, however, 'Kim's Knee High' is unique in its clear pinkish red flower color and extended bloom period. The flowers of the general species range from white and cream to pink, carmine and purple with greenish or bronze colored centers. *Echinacea purpurea* grows in most soils in zones 3 through 9 and is tolerant of high heat and drought.

BRIEF DESCRIPTION OF DRAWINGS

Flowers at various stages of development and overall habit are shown with color as reasonably true as possible with color reproductions.

DETAILED DESCRIPTION OF PLANT VARIETY

Figure 1:
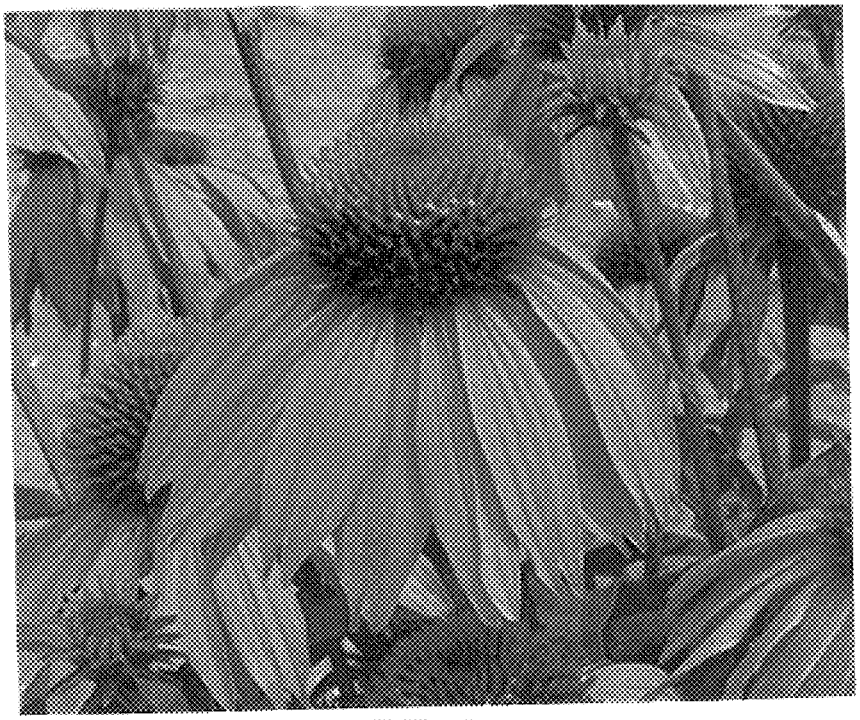
FIG. 1—shows a close-up view of the flowers also in a garden.
Figure 2:
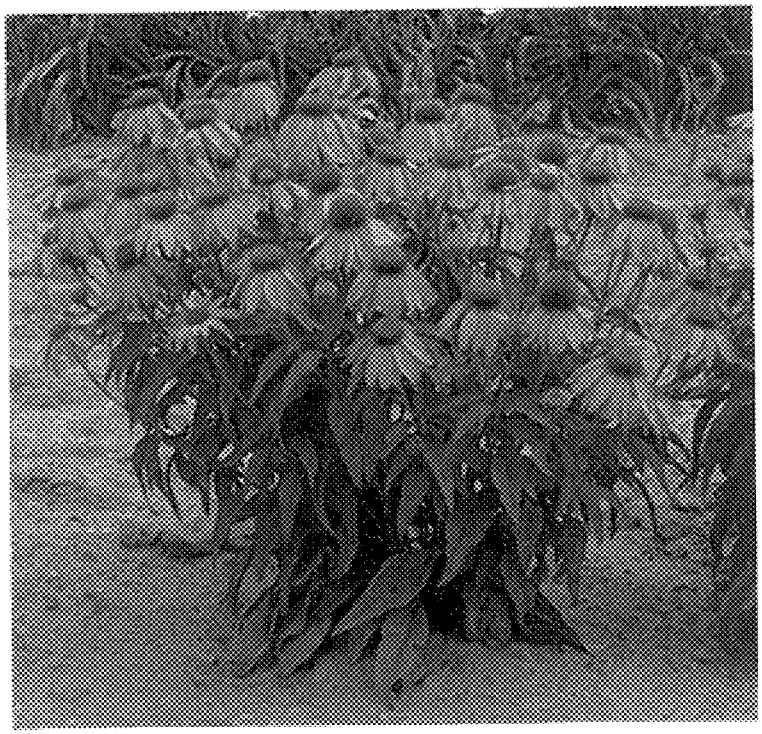
FIG. 2—shows the habit of the plant.

The following color description is based on color terminology in accordance with *The Royal Horticultural Society Colour Chart* and is labeled with R.H.S., and the appropriate code numbers.

Echinacea 'Kim's Knee High' is an herbaceous perennial that is hardy from zone 3 to 9 on the USDA Plant Hardiness Chart. It is both drought and heat tolerant and grows with one to several multiple branched stems from a fibrous rooted crown or caudex. Stems or peduncles are up to 18 inches (45 cm) long and to ¼ inch (6 mm) thick. The stem color is a light yellow green, about R.H.S. 145 B. The stems are hispid to hirsute with basal leaves 1 to 5 times longer than the 3.75 to 7.0 cm (1.5 to 3.0 inches) wide. The stems possess middle cauline leaves in an alternate pattern with usually one or seldom more alternate branches in the upper leaf axils. The leaves are usually found 7 to 8 per stem and are scabrous on both sides, with blades mostly toothed (especially on the lower leaves). Both basal and cauline leaves are attenuate or tapered on the petiole to form a wing, laceolate to lance-ovate. Petioles are the same color as the peduncle, vary in length from about 8 to 15 cm long, and are approximately 5 mm wide. Leaves are between R.H.S. 135 A and 135 B on both the adaxial and abaxial surfaces.

The plant sends out the first set of flowers on peduncles 38 to 45 cm (15 to 18 inches) tall in late June in the Chapel Hill, N.C. area. If cut back after flowering it will send up a second flush of flowers on peduncles 50 to 60 cm (20 to 24 inches) tall about six to eight weeks later in mid August, and will sporadically flower afterwards until frost. Echinacea 'Robert Bloom' U.S. Plant Pat. No. 2,414, with its darker red to carmine-purple flowers, reaches heights of 30 to 38 inches (90 to 97 cm) tall, and most other selections, such as 'Magnus' (not patented) and 'White Swan' (not patented), flower from 90 to 120 cm (36 to 48 inches) tall with some others as tall as 150 cm (60 inches). 'Kim's Knee High' is about one half the height of normal *Echinacea purpurea*. In trial tests at a nursery in Connecticut as well as in North Carolina, *Echinacea purpurea* 'Kim's Knee High' had a prolonged flowering period of twelve weeks or more. Three year old plants of *Echinacea purpurea* 'Kim's Knee High' are 16 to 24 inches (40 to 60 cm) wide.

The flowers of *Echinacea purpurea* 'Kim's Knee High' are solitary heads with up to 24 drooping, mostly bifid, rose pink to purple-pink ray florets (beginning about R.H.S. 61 A and lightening to R.H.S. 67 C), 3.5 to 4.5 cm (1⅓ to 1¾ inches) long and 7 to 10 mm (¼ to ⅜ inches) wide. A three year old plant may have between 45 and 60 flowers at one time, and up to 90 during the entire growing season. Each flower lasts on the plant three to four weeks. The plant has approximately 400 disk florets that are dark bronze (close to R.H.S. 166 A to 166 B) with golden tips (between R.H.S. 17 A and 21 A depending on maturity of florets). Just after opening and before the florets begin drooping the ray florets are darker, in the range of R.H.S. 64 B to 58 C, being darker in the center of the floret, and the disk florets are about a purple R.H.S. 59 A to greyed-purple 187 C. The flower has about 24 to 56 small acute sepals less than 8 mm long and about 2 mm wide. Color of the sepals is nearly identical to the leaves. Approximately two weeks prior to horizontal floret stage the nearly rounded buds are about one inch (2.5 cm) in diameter and the immature florets are about a R.H.S. 151 D. The plant does produce seeds. Seeds, sex organs and a barely detectible floral fragrance are normal for the species. Seeds, typical for the species, are about 5 mm long, about 2 mm wide, and vary from light to medium tan in color. Each flower may have approximately 50 and 125 seeds per flower. Under different environmental conditions, (southern United States versus northern United States), or growing under greenhouse coverings versus garden setting, flower colors may vary slightly but the plant is genotypically stable. Specific siting within the garden as to sun exposure, heat, fertility, water availability, etc. also may affect the flower color, number of flowers per plant and leave sizes, shape and color, slightly. For example, plants grown in heavy shade have longer and more defined petioles with deeper green color, and flower number is reduced.

The plant is drought tolerant, fertile and is not susceptible to any major pathogens.

I claim:

1. A new and distinct dwarf cultivar of *Echinacea purpurea* plant named 'Kim's Knee High', with extended flowering period, developed and discovered in a cultivated state, asexually propagated by the inventor and suitable for landscape or potted plant culture, as herein illustrated and described.

* * * * *